United States Patent [19]

Schlick et al.

[11] Patent Number: 5,277,903

[45] Date of Patent: * Jan. 11, 1994

[54] USE OF TNF AND LT FOR THE PREPARATION OF DRUGS

[75] Inventors: Erich Schlick, Otterstadt; Manfred Kaufmann; Ulrich Raeth, both of Heidelberg, all of Fed. Rep. of Germany

[73] Assignee: Knoll AG, Ludwigshafen, Fed. Rep. of Germany

[*] Notice: The portion of the term of this patent subsequent to Jul. 28, 2009 has been disclaimed.

[21] Appl. No.: 853,517

[22] Filed: Mar. 18, 1992

Related U.S. Application Data

[63] Continuation of Ser. No. 296,144, Jan. 12, 1989, Pat. No. 5,133,960.

[30] Foreign Application Priority Data

Jan. 15, 1988 [DE] Fed. Rep. of Germany ....... 3801026

Oct. 31, 1988 [DE] Fed. Rep. of Germany ....... 3837012

[51] Int. Cl.$^5$ ..................... A61K 45/05; A61K 39/00
[52] U.S. Cl. ................................. 424/85.1; 424/88
[58] Field of Search ....................................... 424/85.1

[56] References Cited

PUBLICATIONS

Berek, et al., 1985, "Intraperitoneal Recombinant α-Interferon . . . " Cancer Research 45:4447–4453.
Malik, et al., 1989, "Paradoxical effects of tumor Necrosis Factor . . . " Ind. J. Cancer 44:918–925.

Primary Examiner—Christine M. Nucker
Assistant Examiner—L. Smith
Attorney, Agent, or Firm—Oblon, Spivak, McClelland, Maier & Neustadt

[57] ABSTRACT

TNF and LT are used for the prophylaxis and therapy of effusions in body cavities.

6 Claims, No Drawings

USE OF TNF AND LT FOR THE PREPARATION OF DRUGS

This is a continuation, of application Ser. No. 07/296,144, filed on Jan. 12, 1989, now U.S. Pat. No. 5,133,960.

TNF (tumor necrosis factor) is a tumor-destroying substance intended for use in controlling malignant tumors. The structure of this substance has been described in Nature 312 (1984), 724. LT (lymphotoxin) is a substance which is related to TNF and has a similar action (Nature 312 (1984), 721). The same applies to muteins of TNF (EP 168,214, EP 205,038, EP 251,037 and WO 86(02381)) and of LT (EP 164,965 and DE 3,620,656).

We have found that these substances are also suitable for the prophylaxis and therapy of effusions in body cavities.

The present invention relates to the use of TNF, LT and their muteins for the preparation of drugs for the prophylaxis and therapy of effusions in body cavities, and the use of TNF for the prophylaxis and therapy of effusions in body cavities.

Effusions are pleural effusions, pericardial effusions, peritoneal effusions (ascites) and hydrarthrosis, which may occur as a result of malignant and nonmalignant diseases. Examples of malignant effusions are, in particular, ascites following ovarial tumors, gastrointestinal tumors, hypernephromas and carcinomas of the breast, and pleural effusions following bronchial carcinomas, mesotheliomas, carcinomas of the breast and hypernephromas. Examples of nonmalignant effusions are, in particular, ascites following liver diseases, for example cirrhosis of the liver, virus-related pleural and pericardial effusions and hydrarthrosis in the case of inflammatory and/or degenerative joint diseases.

Since TNF, LT and their muteins are proteins which are destroyed in the gastrointestinal tract, they can only be administered parenterally, preferably intravenously, intraperitoneally, intrapleurally and intraarticularly. Sterile isotonic solutions are suitable for this purpose. These can be prepared, for example, by dissolving the protein in a blood-isotonic aqueous solution, subjecting the solution to sterile-filtration and filling it into ampoules. The pH of the solution is preferably from 5 to 8, in particular about 7.5.

The dose to be administered per patient is from 10 to 1,000 μg, preferably from 30 to 700 μg, of protein per $m^2$ of body area. This dose is administered once or twice a week for a duration of treatment of from 1 to 6 weeks. The treatment cycle can be repeated several times if required.

The efficacy of TNF, LT and their muteins can be illustrated as follows, using TNF as an example:

12 patients suffering from malignant ascites following overial carcinomas and 10 patients suffering from malignant ascites following gastrointestinal tumors received an intraperitoneal infusion of TNF once a week in doses of from 20 to 200 μg per $m^2$ of body area over a period of from 1 to 6 weeks. After the treatment, none of the 12 patients with ovarial carcinomas had detectable malignant ascites. Of the 10 treated patients with gastrointestinal tumors, 7 no longer had ascites after the treatment.

Preparation of an administration form 100 mg of TNF are dissolved in 300 ml of 20 mM sodium phosphate buffer of pH 7.5. The solution is rendered blood-isotonic with sodium chloride. 1 g of human serum albumin is added, after which the mixture is sterile-filtered over a pore filter (pore size 0.1–0.2 μm). 3 ml portions are filled into ampoules under sterile conditions.

The ampoules thus obtained can be used directly for injection or can be further diluted by addition to a blood-isotonic solution containing 0.25% of human serum albumin and then infused.

We claim:

1. A method for treating ascites in human body cavities comprising: parenterally administering an effective amount of a pharmaceutical agent consisting essentially of TNF, LT or their muteins to a human suffering from ascites which occur as a result of a malignant disease.

2. A method for treating ascites in human body cavities comprising: parenterally administering an effective amount of a pharmaceutical agent consisting essentially of TNF to a human suffering from ascites which occur as a result of malignant disease.

3. The method of claim 1 wherein the pharmaceutical agent is administered intraperitoneally.

4. The method of claim 1 wherein the pharmaceutical agent is administered intrapleurally.

5. The method of claim 2 wherein the pharmaceutical agent is administered intraperitoneally.

6. The method of claim 2 wherein the pharmaceutical agent is administered intrapleurally.

* * * * *